(12) United States Patent
Ohmiya et al.

(10) Patent No.: US 8,143,013 B2
(45) Date of Patent: Mar. 27, 2012

(54) VISIBLE TO NEAR-INFRARED LIGHT PROBE USING ENERGY TRANSFER BETWEEN LUCIFERASE AND AN ORGANIC DYE VIA A SUGAR CHAIN

(75) Inventors: Yoshihiro Ohmiya, Ikeda (JP); Chun Wu, Ikeda (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 780 days.

(21) Appl. No.: 12/222,356

(22) Filed: Aug. 7, 2008

(65) Prior Publication Data

US 2009/0047219 A1    Feb. 19, 2009

(30) Foreign Application Priority Data

Aug. 14, 2007  (JP) ................. 2007-211216

(51) Int. Cl.
 *C12Q 1/66* (2006.01)
 *C12N 9/02* (2006.01)
 *A61K 49/00* (2006.01)
(52) U.S. Cl. .............................. 435/8; 424/9.6; 435/189
(58) Field of Classification Search ............... 424/9.6; 435/8, 189
See application file for complete search history.

(56) References Cited

U.S. PATENT DOCUMENTS

| | | | | |
|---|---|---|---|---|
| 5,837,465 A | * | 11/1998 | Squirrell et al. | 435/6.12 |
| 6,342,379 B1 | * | 1/2002 | Tsien et al. | 435/173.4 |
| 2007/0254311 A1 | * | 11/2007 | Alagic et al. | 435/7.5 |
| 2008/0038686 A1 | * | 2/2008 | Nagai | 433/29 |

FOREIGN PATENT DOCUMENTS

| | | |
|---|---|---|
| EP | 1 956 086 | 8/2008 |
| WO | 2006/106752 | 10/2006 |
| WO | 2007/058140 | 5/2007 |

OTHER PUBLICATIONS

Park et al. 2005. Multimodality Radionuclide, fluorescence, and Bioluminescence Small-Animal Imaging. Proceedings of the IEEE, vol. 93, No. 4, pp. 771-783.*
Wu, C. et al. 2009. In vivo far-red luminescence imaging of a biomarker based on BRET from Cypridina bioluminescence to an organic dye. PNAS, vol. 106, No. 37, pp. 155599-15603.*
Zhang et al. 2006. Halo-Tag Protein-mediated Site-specific Conjugation of Bioluminecent Proteins to Quantum dots. Angew. Chem., International Edition, vol. 45, pp. 4936-4940.*
Jablonski, E. 1985. The Preparation of Bacterial Luciferase Conjugates for Immunoassay and Application to Rubella antibody Detection. Analytical Biochemistry, vol. 148, pp. 199-206.*
So, Min-Kyung et al. Self-illuminating Quantum Dot Conjugates for In Vivo Imaging. *Nature Biotechnology*, vol. 24, No. 3, Mar. 2006, pp. 339-343.

* cited by examiner

*Primary Examiner* — Jon P Weber
*Assistant Examiner* — Kailash C Srivastava
(74) *Attorney, Agent, or Firm* — Wenderoth, Lind & Ponack, L.L.P.

(57) ABSTRACT

An object of the present invention is to produce a luminescent probe that has less biological effects, efficiently emits visible to near-infrared light, which is excellent for the imaging of individuals, and the use thereof. The present invention provides a sugar chain-containing-luciferase derivative, wherein an organic fluorescent dye is bonded to the luciferase through the sugar chain.

5 Claims, 1 Drawing Sheet

VISIBLE TO NEAR-INFRARED LIGHT PROBE USING ENERGY TRANSFER BETWEEN LUCIFERASE AND AN ORGANIC DYE VIA A SUGAR CHAIN

TECHNICAL FIELD

The present invention relates to a luciferase derivative linked to an organic fluorescent dye via its sugar chain, a complex of the derivative and a bioactive substance, and use of these for

BACKGROUND ART

In the field of life science, it is very important to analyze various cellular phenomena such as changes in the amount of cellular calcium, phosphorylation of intracellular proteins, distribution of ATP, which is a source of energy, transcriptional activities of genes and the like. Various types of molecular probes have been created and used for imaging. These imaging technologies are used for observations at various levels from living cells to organisms. For example, labeling and imaging cancer cells enables the evaluation of anticancer agents and visual analysis of cancer metastases. Light probes, in contrast to radioactive probes, which can be used only by qualified researchers in strictly controlled facilities, have attracted attention. Light probes are broadly divided into luminescent probes and light probes, not requiring use in controlled facilities, nor expensive measuring devices. These probes are stable and inexpensive, and are easily handled. Among light probes, fluorescent probes require excitation light, raising difficulties in obtaining information from deep inside individuals where external light sources cannot be used for excitation. Cellular photodamage caused by external lights also presents a problem. On the other hand, luminescent probes are self-luminescent, not requiring excitation light. Various types of probes have been produced and used for imaging at the individual level.

Luciferase probes are the most utilized among luminescent probes, among which beetle luciferases have already been utilized for intracellular imaging and are found to be useful as a visualization probe enabling prolonged imaging (WO 2007/058140, WO 2006/106752). However, the maximum emission wavelength is 535 nm, in contrast with the most suitable wavelengths for imaging individuals: 650-750 nm, which has very low light energy. Cypridina luciferase makes highly useful probes in combination with its luciferin analogues or nano quantum dots, being capable of producing light with a maximum emission wavelength between about 380 nm (near ultraviolet light, Japanese Patent Application No. 2005-169768) and 650 nm (red to near-infrared light with high penetration efficacy at depth in individuals, US 60/907234). It is clear that, particularly, a near-infrared luminescent probe utilizing energy transfer(bioluminescence resonance energy transfer) between a Cypridina luciferase and nano quantum dot conjugate produces light with high permeability in individuals, thereby making a method using such a probe effective. However, the problems of safety and toxicity or the disturbance of life information caused by luminescent probes associated with the imaging of individuals, such as nano quantum dots using biologically toxic metals and not being easily excreted in the liver, and the like, have been pointed out. Moreover, near-infrared luminescent probes comprising a Renilla luciferase and nano quantum dot conjugate have been reported (So M K et al. Nat Biotechnol. 24 (2006) :339-43), raising concerns about safety for the above reasons.

[Patent document 1] WO2007/058140
[Patent document 2] WO2006/106752
[Patent document 3] Japanese Patent Application No. 2005-169768
[Patent document 4] US60/907,234
[Non-patent document 1] So M K et al. Nat. Biotechnol. 2006, 24:339-43

DISCLOSURE OF THE INVENTION

Problems to be Solved by the Invention

An object of the present invention is to provide and use a luminescent probe that has less adverse effects on living bodies and efficiently emits visible to near-infrared light, which is excellent for the imaging of individuals.

Another object of the present invention is to provide a system in which luciferase is capable of emitting high energy visible to ultraviolet light in a luciferase-organic fluorescent dye complex, and thereby efficiently exciting the organic fluorescent dye via sugar chains on the protein.

Means for Solving the Problems

The present inventors conducted extensive research to solve the above problems, and, as a result, found that excitation light with high energy can be produced by constructing a derivative having Cypridina luciferase linked to an organic fluorescent dye via its sugar chain and, and using luciferin or an analogue thereof, thereby accomplishing the present invention.

The present invention provides a luciferase derivative, a labeled bioactive substance, a biological imaging method, and use of a visible to near-infrared light probe thereof.

1. A luciferase derivative, wherein the luciferase contains a sugar chain; and the sugar chain mediates linkage of an organic fluorescent dye to the luciferase.

2. The derivative according to Item 1, wherein the luciferase is Cypridina luciferase.

3. The derivative according to Item 1 or 2, wherein the derivative has a fluorescence maximum in the range of 650 nm and 750 nm by irradiation from bioluminescence resonance energy transfer between the organic fluorescent dye and the luciferase.

4. The derivative according to any one of Items 1 to 3, wherein the organic fluorescent dye has a fluorescence maximum ($\lambda_{max}$) in the range of 400 nm and 700 nm resulting from an external excitation light source.

5. The derivative according to any one of Items 1 to 4, wherein the organic fluorescent dye is any one of compounds having a skeletal structure of indocyanine green, coumarin, rhodamine, xanthene, hematoporphyrin, or fluorescamine.

6. The derivative according to any one of Items 1 to 4, wherein the organic fluorescent dye is any one of compounds having a skeletal structure of indocyanine green, coumarin, rhodamine, xanthene, hematoporphyrin, or fluorescamine; and the compound has a radioactive element introduced therein.

7. A labeled bioactive substance that is labeled with the luciferase derivative according to any one of Items 1 to 6.

8. The labeled bioactive substance according to Item 7, wherein the bioactive substance is at least one species selected from the group consisting of antibodies, antigens, haptens, hormones, ligands for receptors or ion channels, sugar chains and nucleic acids.

9. The labeled bioactive substance according to Item 7 or 8, wherein the bioactive substance is recognized by a cell.

10. The labeled bioactive substance according to any one of Items 7 to 9, wherein the organic fluorescent dye is linked to luciferase via a sugar chain of the luciferase to link the peptide portion of the luciferase and the bioactive substance.

11. The bioactive substance according to Item 10, wherein the luciferase is a Cypridina luciferase.

12. The biological imaging method comprising the steps of applying a bioactive substance labeled with Cypridina luciferase and an organic fluorescent dye to a living body; the bioactive substance being at least one species selected from the group consisting of antibodies, antigens, haptens, hormones, ligands for receptors and ion channels, sugar chains and nucleic acids, and detecting a fluorescence maximum in the range of 650 nm and 750 nm resulting from energy transfer between the Cypridina luciferase and the organic fluorescent dye.

13. Use of the luciferase derivative of any one of Items 1 to 6 or the labeled bioactive substance of any one of Items 7 to 11, as a visible to near-infrared light probe for a bioactive substance.

Effects of the Invention

According to the present invention, luciferase, particularly Cypridina luciferase, can emit visible to near-infrared-containing light. The luciferase can effectively excite an organic fluorescent dye by linking the dye to luciferase via a sugar chain in appropriate position for bioluminescence resonance energy transfer. Luciferase derivatives of the present invention are luminescent probes with the size of proteins, and are safe. On the other hand, sugar-chain-containing luciferases such as Cypridina luciferase and the like, that can be linked to peptides or proteins (for example, antibodies, antigens, haptens, hormones and the like) via sugar chain, can also accumulate in cancer tissues, allowing individual imaging of cancer tissues using near-infrared light, and enabling application to the treatment of various types of clinical conditions and the development of new drugs. Further, such luciferase derivatives can also be applied for photodynamic therapy using a broad range of emission wavelengths.

For transgenic cells into which the previously known firefly luminescence enzymes have been introduced, the amount of luminescence emitted was not sufficient for luminescence imaging using near-infrared light. Luciferase-quantum dot complexes are near-infrared light probes of a poorly excretable size, and so the biological effects of such metal dots have been of concern. A luciferase-organic fluorescent dye complex of the present invention is, when introduced in vivo, capable of more efficiently emitting visible to near-infrared light compared with previously used luciferase-quantum dot complexes, avoiding toxicity to organisms due to size and material, and enabling the imaging of organs deeper inside individuals for a long period of time.

BEST MODE FOR CARRYING OUT THE INVENTION

The luciferase used in the present invention is not particularly limited so long as the luciferase has sugar chains to link an organic fluorescent dye, and further to link a bioactive substance. Preferable examples of such luciferases include Cypridina luciferases. The luciferases need to have sugar chains. Thus, luciferases expressed in eukaryotic cells such as yeast, insect cells, mammalian cells such as CHO cells, and the like are preferably used.

Examples of the organic fluorescent dyes include, but are not limited to, any of those having sugar chain-linkable amino groups or hydrazino groups (NH$_2$NH—), and causing bioluminescence resonance energy transfer with luciferase and emitting visible to near-infrared light, preferably light with a wavelength between about 650 to 750 nm. The fluorescence maximum ($\lambda_{max}$) of the organic fluorescent dyes may be between about 400 to 700 nm, preferably about 400 to 500 nm. Examples of preferable organic fluorescent dyes include any compounds having the skeletal structure of indocyanine, coumarin, rhodamine, xanthene, hematoporphyrin, fluorescamine, and the like, with cyanine dyes such as an indocyanine green and derivatives thereof being more preferable.

Examples of the bioactive substances include antibodies, antigens, haptens, hormones, ligands for receptors or ion channels, sugar chains, nucleic acids and the like. The antibodies may be any of monoclonal antibodies and polyclonal antibodies. Examples of the antibodies include, for example, when applied to humans, humanized antibodies or their fragments. Examples of the nucleic acids include substances capable of recognizing bioactive substances such as aptamers. Examples of antigens include those linkable to receptors on immunocytes or cells in vivo. Examples of hormones include peptide hormones, steroid hormones, and various types of growth hormones. Examples of ligands for receptors or ion channels include nicotine, glutamic acid, serotonin, and the like. The sugar chains include those recognized by organisms or cells, such as sialyl Lewes X and derivatives thereof.

In one of the preferred embodiments of the present invention, the amount of luminescence emitted from the Cypridina luciferase-organic fluorescent dye complex and luciferin is, for example, at least 2 times, preferably at least 4 times, more preferably at least 10 times, compared with the amount of luminescence emitted from the combination of Cypridina luciferase and a quantum dot. According to the present invention, the toxicity of nano metallic dots can also be avoided.

The Cypridina luciferase used in the present invention is known. In the specification and claims of the present invention, the term "Cypridina luciferase" includes wild type Cypridina luciferases and any mutants thereof. The amino acid sequences of wild type Cypridina luciferases are registered under AAB86460, AAA30332, BAD08210 and the like.

Examples of modified Cypridina luciferase variants include any of those with one or multiple amino acids, preferably one to a few amino acids, preferably one to a dozen amino acids (for example, 2, 3, 4, 5, 6, 7, 8, 9, 10, 11, 12, 13, 14, or 15 amino acids) substituted, added, deleted or inserted, and include any variants that have luminescence activity when Cypridina luciferin is used as a substrate. Such mutants have a homology of at least 70% with the wild-type Cypridina luciferase above, preferably at least 80%, more preferably at least 90%, even more preferably at least 95%, particularly even more preferably at least 98%, or most preferably at least 99%.

Such luciferase variants can be produced according to a known method, by, for example, naturally occurring luciferase being modified by site specific mutagenesis (Methods in Enzymology 154 (1987): 350 and 367-382; Methods in Enzymology 100 (1983): 468; "genetic-research method II" New Biochemistry Experiment Lectures 1 (1986): 105) and the like; mutated DNA being synthesized by a chemical synthesis such as the phosphotriester method or the phosphoric acid aminodite method (J. Am. Chem. Soc. 89 (1967): 4801; J. Am. Chem. Soc. 91 (1969): 3350; Science 150 (1968): 178; Tetrahedron Lett. 22 (1981): 1859; Tetrahedron Lett. 24 (1983): 245), or by a combination of these methods.

Amino acid sequence identity or homology (%) can be determined using conventional programs (for example, BLAST, FASTA, and the like) at their default settings. The identity (%) can also be determined using a known algorithm in the field, for example, the algorithm of Needleman et. al. (J. Mol. Biol. 48 (1970): 444-453), the algorithm of Myers and Miller (CABIOS 4 (1988): 11-17), and the like. The algorithm of Needleman et. al. is integrated in the GAP program of the GCG software package (available at www.gcg.com). The identity (%) can be determined using, for example, any of BLOSUM 62 matrix or PAM 250 matrix, and a gap weight of: 16, 14, 12, 10, 8, 6, or 4; and any one of length weight: 1, 2, 3, 4, 5, or 6. The algorithm of Myers and Miller is integrated in the ALIGN program, which is part of the GCG sequence alignment software package. When the ALIGN program is used to compare amino acid sequences, for example, PAM 120 weight residue table, a gap length penalty of 12 and a gap penalty of 4 can be used. The amino acid identity can be any of those determined by a method above. For example, for the calculation, among the above, the method producing the lowest value can be employed.

Sugar chain-containing luciferase is linked to an organic fluorescent dye, for example, as follows. A luciferase sugar chain is treated with a periodate, such as $NaIO_4$, cleaving the vicinal diol of the sugar chain to produce an aldehyde. With this, an amino group or a hydrazino group ($NH_2NH$—)-containing organic fluorescent dye undergoes a reaction. In the case of linking to an amino group in the dye, a reducing agent such as $NaBH_3CN$ or the like is used as needed. Thus, a luciferase derivative with an organic fluorescent dye linked to the sugar chain portion can be obtained.

One example of the reaction scheme, in which an organic fluorescent dye (organic dye) is introduced to Cypridina luciferase, is presented below.

Chemical Formula 1

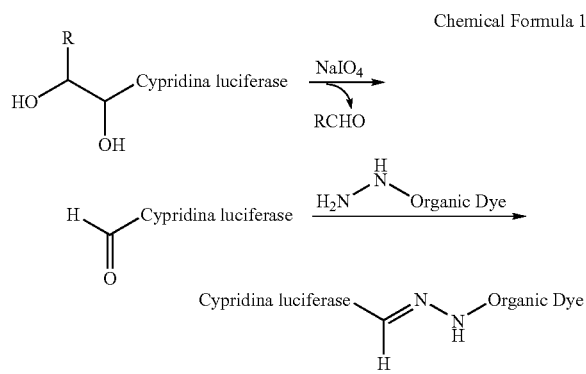

Luciferase is dissolved in an appropriate buffer, such as acetate buffer, mixed with one equivalent amount or an excess amount of $NaIO_4$ solution, and left to react at a low temperature such as 4° C. to room temperature for ten minutes to three hours, and then subjected to post-treatment, such as column purification and the like, as needed, to produce aldehyde group-containing luciferase. The resulting luciferase is reacted with an organic fluorescent dye-$NHNH_2$ compound (equivalent, excess, or stoichiometric amount), to obtain a luciferase derivative of the object compound, in which the organic fluorescent dye is linked.

In the above reaction, luciferase is reacted with $NaIO_4$ solution such that at least two molecules of aldehyde will be present in one molecule of luciferase, and then reacted with an organic fluorescent dye-$NHNH_2$ compound such that at least one molecule of aldehyde residue remains unreacted per one molecule of luciferase. Subsequently, the resultant is reacted with an amino group-containing bioactive substance, and treated with a reducing agent such as $NaBH_3CN$, to further produce an organic fluorescent dye-luciferase-bioactive substance complex. Alternatively, the organic fluorescent dye-linked luciferase derivative is re-reacted with a $NaIO_4$ solution to generate an aldehyde group. Subsequently, the resultant is reacted with an amino group-containing bioactive substance, and reacted with a reducing agent such as $NABH_3CB$ or the like, to further produce an organic fluorescent dye-luciferase-bioactive substance complex.

Said sugar chain mediated organic fluorescent dye introduction can be applied to luciferase derivatives. Luciferase derivatives are luciferases in which bioactive substances are linked to their active reaction groups directly or via cross-linking agents; or luciferases in which peptide sequences are inserted at the N-terminus and the C-terminus of the luciferase.

Examples of linking luciferase and a bioactive substance include activating a COOH group of the luciferase using a condensing agent such as dicyclohexylcarbodiimide or the like, and then coupling the activated COOH group with an amino group. Another example of a linking method includes linking using a bivalent or a multivalent cross-linking agent. Examples of cross-linking agents include those having at least two linkable reaction groups, such as a maleimide group, a succinimide group, an active ester group, a hydrazine group, and the like; and to these groups, a bivalent or muitivalent group such as alkylenes, arylenes, alkenylenes, polyoxyethylenes, polyoxypropylenes or the like, are linked. Examples of cross-linking agents include AEDP, AMAS, APG, ASBA, BASED, BMB, BMDB, DTSSP, EMCA, EMCH, EMCS, HBVSKMUA, SADP, SAED and the like. Such a cross linking agent can be selected depending on the reactive group (an amino group, a SH group, a OH group, an aldehyde group, a ketone group, or the like) of the bioactive substance. The cross-linking agents are preferably heterobifunctional, and capable of linking luciferase and an active substance stepwise. Examples of peptide sequences inserted at the C-terminus and the N-terminus of luciferase include HaloTag®, Avi-Tag, SNAPTag®, antibodies and fragments thereof.

There is bioluminescence resonance energy transfer (BRET) between the organic fluorescent dye and luciferase. This gives luminescence in the range of visible to near-infrared light between 650 and 750 nm, allowing biological imaging. Due to this energy transfer, the organic fluorescent dye may be of those with a fluorescence maximum $\lambda_{max}$ between about 400 nm to 700 nm, for example, about 400 nm to 550 nm, or about 420nm to 500 nm.

EXAMPLES

The present invention will be described more specifically with reference to Examples below, however it is not limited to these Examples.

Example 1

1. Introduction of Dye into the Cypridina Luciferase Sugar Chain

Chemical Formula 2

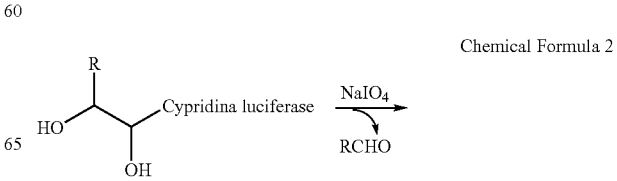

-continued

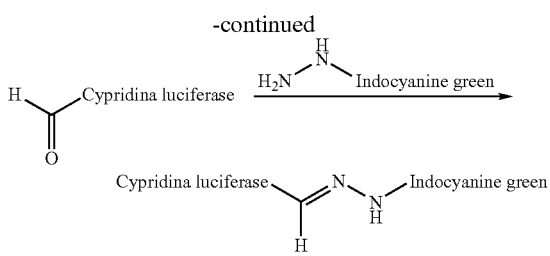

A 0.1 mg parts quantity of purified luciferase was dissolved in 0.05 ml of 0.1M acetate buffer with a pH of 5.2, mixed with the equivalent amount of 0.1 M acetate buffer of 20 mM NaIO$_4$ with a pH of 5.2, and gently stirred at 4° C. for 0.5 hour. The reaction mixture was placed on a PD-10 column (product of GE Health), and eluted with a solution of 100 mM sodium phosphate and 150 mM NaCl. Only the active fractions were collected (about 2 mL). Using Biomax 100K of Millipore Corp., each 2 mL solution was concentrated to 0.02 ml. A 1 mg parts quantity of Hilyte fluore™ 647 (NH$_2$NH-indocyanine green; Anaspec) was dissolved in 0.1 ml of 0.1 M acetate buffer with a pH of 5.2. A 0.02 ml parts quantity of the solution was reacted with the equivalent amount of the luciferase mixture at room temperature for two hours. The reaction mixture was placed on a PD-10 column (product of GE Health, and eluted with a solution of 100 mM sodium phosphate and 150 mM NaCl. Only the active fractions were collected (about 2 mL).

2. Emission Spectrum of Cypridina Luciferase-Organic Fluorescent Dye

A 0.001 ml parts quantity of Cluc-dye was dissolved in 0.1 ml of each of the buffers below, then reacted with 0.001 ml of Cypridina luciferin mixture (0.001 mM), and the emission spectrum was measured. The results are shown in FIGS. 1 and 2.

0.1 M Phosphate buffer pH 6.4/100 mM NaCl
    0.1 M Phosphate buffer pH 7.4/100 mM NaCl
    0.1 M Tris-HCl buffer pH 8.0/100 mM NaCl
    0.1 M Phosphate buffer (0.1 M) pH6.4/500 mM NaCl
    0.1 M Phosphate buffer (0.1 M) pH7.4/500 mM NaCl
    0.1 M Tris-HCl buffer pH 8.0/500 mM NaCl As a result, a maximum emission wavelength of luciferase (460 nm) and a maximum emission wavelength of the dye (670 nm) resulting from the energy transfer of the emissions were observed. Further, it was found that these emission spectra were not affected by changes in conditions such as the salt concentrations, pH, or the like.

Figure 1:
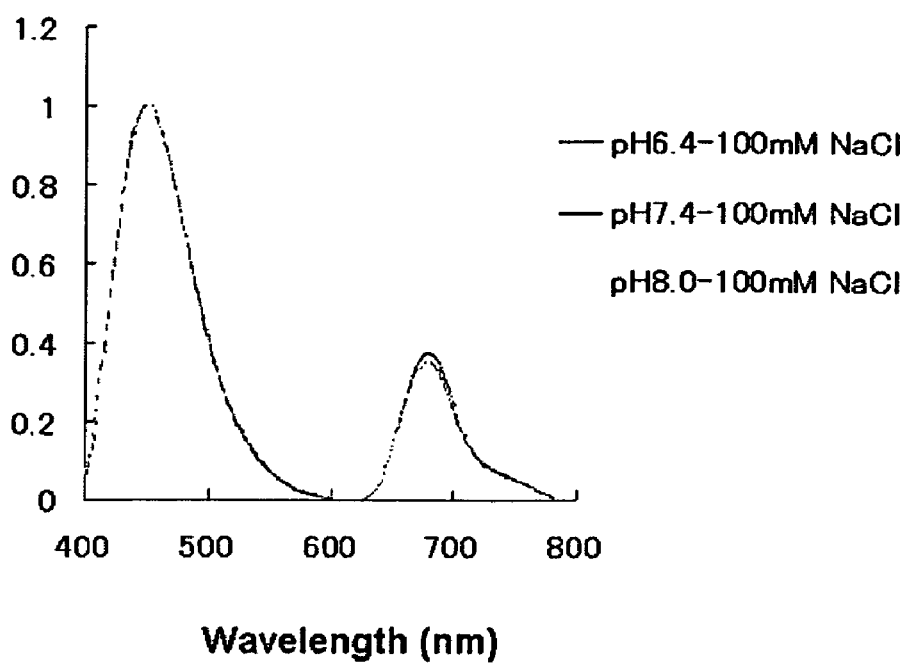
FIG. 1 shows the emission spectrum of Cypridina-fluorophore.
Figure 2:
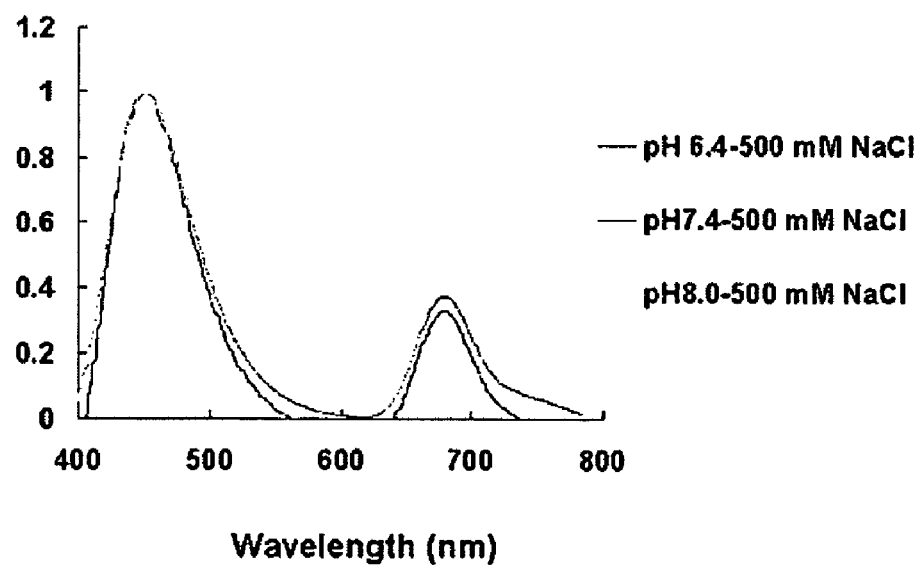
FIG. 2 shows the emission spectrum of Cypridina-fluorophore.

The invention claimed is:

1. A biological imaging method comprising the steps of applying a bioactive substance labeled with Cypridina luciferase and an organic fluorescent dye to a living body; the bioactive substance being at least one species selected from the group consisting of antibodies, antigens, haptens, hormones, ligands for receptors and ion channels, and detecting a fluorescence maximum in the range of 650 nm and 750 nm resulting from bioluminescence resonance energy transfer between the Cypridina luciferase and the organic fluorescent dye, wherein the organic fluorescent dye has a fluorescence maximum ($\lambda$max) in the range of 400 nm and 700 nm by irradiation from an external excitation light source, wherein said organic fluorescent dye is bonded to Cypridina luciferase through the sugar chain of Cypridina luciferase and wherein said bioactive substance are linked together.

2. The biological imaging method according to claim 1, wherein the organic fluorescent dye has a fluorescence maximum ($\lambda$max) in the range of 400 nm and 500 nm by irradiation from an external excitation light source.

3. The biological imaging method according to claim 1, wherein the organic fluorescent dye has the skeletal structure of indocyanine or xanthene.

4. The biological imaging method according to claim 1, wherein the organic fluorescent dye is indocyanine green.

5. The biological imaging method according to claim 1, wherein the organic fluorescent dye is linked to luciferase via a sugar chain of the luciferase to link the peptide portion of the luciferase and the bioactive substance.

* * * * *